(12) United States Patent
Eighmy et al.

(10) Patent No.: US 11,147,609 B2
(45) Date of Patent: Oct. 19, 2021

(54) SURGICAL CUTTING DEVICE

(71) Applicant: Fulmer Instruments, LLC, Mountain Brook, AL (US)

(72) Inventors: Eugene A Eighmy, Mountain Brook, AL (US); Benjamin B Fulmer, Mountain Brook, AL (US); Lloyd G. B. Cooper, Mountain Brook, AL (US)

(73) Assignee: Fulmer Instruments, LLC, Mountain Brook, AL (US)

( * ) Notice: Subject to any disclaimer, the term of this patent is extended or adjusted under 35 U.S.C. 154(b) by 312 days.

(21) Appl. No.: 16/440,726

(22) Filed: Jun. 13, 2019

(65) Prior Publication Data

US 2019/0328444 A1 Oct. 31, 2019

Related U.S. Application Data

(62) Division of application No. 14/608,390, filed on Jan. 29, 2015, now Pat. No. 10,363,085.

(60) Provisional application No. 61/933,611, filed on Jan. 30, 2014.

(51) Int. Cl.
*A61B 18/12* (2006.01)
*A61B 18/14* (2006.01)
*A61B 18/00* (2006.01)

(52) U.S. Cl.
CPC ...... *A61B 18/1233* (2013.01); *A61B 18/1402* (2013.01); *A61B 2018/00589* (2013.01); *A61B 2018/00601* (2013.01); *A61B 2018/00732* (2013.01); *A61B 2018/00767* (2013.01); *A61B 2018/00845* (2013.01); *A61B 2018/00892* (2013.01); *A61B 2018/1412* (2013.01)

(58) Field of Classification Search
CPC ............ A61B 18/1233; A61B 18/1402; A61B 2018/00589; A61B 2018/00601; A61B 2018/00732; A61B 2018/00867; A61B 2018/00845; A61B 2018/00892; A61B 2018/1412
See application file for complete search history.

(56) References Cited

U.S. PATENT DOCUMENTS

| | | | |
|---|---|---|---|
| 4,878,493 | A | 11/1989 | Pasternak |
| 5,133,711 | A | 7/1992 | Hagen |
| 5,792,138 | A | 8/1998 | Shipp |

(Continued)

*Primary Examiner* — Michael F Peffley
*Assistant Examiner* — Tigist S Demie
(74) *Attorney, Agent, or Firm* — Paul Sykes; Jake M. Gipson; Bradley Arant Boult Cummings LLP

(57) ABSTRACT

A cordless surgical knife comprises an enclosure and a blade extending from the enclosure. The enclosure contains a differential amplifier circuit configured to provide an RF signal, an output monitor feedback circuit, a return monitor feedback circuit, and a microprocessor that receives data from the feedback circuits and adjusts the RF signal. The enclosure contains a receiving antenna that is operable to receive a wireless signal associated with the RF signal from tissue of a patient. A transmitting antenna may be in electrical contact with tissue of the patient and transmit the wireless signal. Optionally, both the receiving antenna and transmitting antenna include at least two separate inductive circuits aligned on different planes, or each of the receiving antenna and the transmitting antennas is encapsulated inside an enclosure floating in a liquid so that the antennas are aligned by gravity.

20 Claims, 8 Drawing Sheets

(56) References Cited

U.S. PATENT DOCUMENTS

| | | |
|---|---|---|
| 6,039,734 A | 3/2000 | Goble |
| 6,464,696 B1 | 10/2002 | Oyama et al. |
| 6,551,312 B2 | 4/2003 | Zhang et al. |
| 6,569,163 B2 | 5/2003 | Hata et al. |
| 7,247,155 B2 | 7/2007 | Hoey et al. |
| 7,666,182 B2 | 2/2010 | Klett et al. |
| 7,842,033 B2 | 11/2010 | Isaacson et al. |
| 7,901,400 B2 | 3/2011 | Wham et al. |
| 8,002,769 B2 | 8/2011 | Goble et al. |
| 8,105,323 B2 | 1/2012 | Buysse et al. |
| 8,226,639 B2 | 7/2012 | Podhajsky et al. |
| 8,231,616 B2 | 7/2012 | McPherson et al. |
| 8,267,928 B2 | 9/2012 | Orszulak et al. |
| 8,377,054 B2 | 2/2013 | Gilbert |
| 8,377,059 B2 | 2/2013 | Deville et al. |
| 2011/0115562 A1 * | 5/2011 | Gilbert ................ H03F 3/2171 330/262 |
| 2011/0118729 A1 | 5/2011 | Heeren et al. |
| 2011/0288543 A1 | 11/2011 | Cheng |
| 2012/0136347 A1 | 5/2012 | Brustad |
| 2013/0035679 A1 | 2/2013 | Orszulak |

\* cited by examiner

SURGICAL CUTTING DEVICE

CROSS-REFERENCE TO RELATED APPLICATIONS

This application is a divisional of U.S. application Ser. No. 14/608,390, now U.S. Pat. No. 10,363,085, entitled "Surgical Cutting Device" and filed on Jan. 29, 2015, which claims the benefit of and priority to U.S. Provisional Patent Application No. 61/933,611 entitled "Cordless Surgical Cutting Device" and filed on Jan. 30, 2014. The contents of U.S. application Ser. No. 14/608,390, now U.S. Pat. No. 10,363,085, are incorporated herein by reference in their entirety.

FIELD OF THE INVENTION

The invention relates generally to medical devices. More specifically, the present invention relates to a surgical cutting device.

BACKGROUND

Electronic surgical instruments are well known have been used for cutting and coagulating tissue in a surgical environment since the mid-twentieth century. A typical electronic instrument of this type includes a controller that is wired to the patient and also wired to the cutting tip of the instrument. However, the wire that connects the controller and the cutting tip limits freedom of movement by the surgeon. Additionally, the wire may affect the precision and the position of the incision. Finally, the wire may also be a source of contamination that will require additional sterilization procedures. Consequently, a need exists for an improved surgical cutting device.

SUMMARY OF THE INVENTION

One embodiment of the invention relates to a surgical apparatus, comprising: a blade with an edge for contacting tissue of a patient; a differential amplifier circuit configured to provide a signal having a voltage and a current to the blade at a certain frequency and waveform; an output monitor feedback circuit that monitors frequency and amplitude data from the differential amplifier circuit; a return monitor feedback circuit that monitors that monitors frequency and amplitude data from the tissue; and a microprocessor that receives the frequency and amplitude data from the output monitor and from the return monitor and adjusts at least one of the voltage, frequency and waveform provided by the differential amplifier Another embodiment of the invention relates to a surgical apparatus, comprising: a cordless surgical apparatus, comprising: a blade with a surface edge for contacting tissue of a patient, where the blade is operably coupled to a receiving antenna; a signal amplifier with a transmitting antenna that transmits a signal to the receiving antenna at a certain frequency and waveform; an output monitor feedback circuit that monitors frequency and amplitude data from a differential amplifier circuit; a return monitor feedback circuit that monitors that monitors frequency and amplitude data from the tissue of the patient; and a microprocessor that receives the frequency and amplitude data from the output monitor and from the return monitor and adjusts the voltage, frequency and waveform provided by the differential amplifier.

Other aspects and advantages of the invention will be apparent from the following description and the appended claims.

BRIEF DESCRIPTION OF DRAWINGS

It should be noted that identical features in different drawings are shown with the same reference numeral.

DETAILED DESCRIPTION

A cordless surgical cutting device has been developed. One embodiment of the present invention operates as a surgical tool that cuts tissue without the use of a cord or wire. In this embodiment, the cutting device is battery powered with a microprocessor that allows precise adjustment of frequencies and pulse widths of the current of the device. The current loop of the device is completed using electrostatic coupling from the surface of the patient's skin, through the air, and back to an antennae/receiver in the hand-held cordless device.

During operation, the device applies power to the tip of a modular cutting surface or "blade" sufficient to non-thermally cauterize, cut, singe, or burn tissue. One component of the device is an antennae/receiver which facilitates a tuned circuit matched to the tip frequency that provides electrostatic coupling to tissue, as shown in the figures. Some embodiments of the present invention also have the ability to monitor current with sufficient precision to discern between different tissue types (based on the respective impedance) and to shut off current or warn a user if the blade is contacting a non-desired tissue type.

In addition, a conductive pad with a frequency matched to the tuned circuit and antennae may be affixed to the patient to further enhance the electrostatic coupling. The use of the tuned circuit, antenna or copper pad, and conductive pad affixed to patient provides a return path for the knife current thus eliminating the need for wires which are required in existing surgical knife systems.

A preferred embodiment of the present invention, for use with surgery on human tissue, may operate with a current of 2-10 milliamps and a voltage of 1000-3000 volts. During operation, the current may be lowered while the voltage is adjusted correspondingly to maintain a desired power level. The device may operate at a frequency of 400 kHz. In some embodiments, the device to operates across the RF spectrum to take advantage of increased efficiencies in size and power transfer. For example, the present device may adjust the operating frequency for maximum power transfer or for a specific type of tissue. However, the device when intended for use with surgery on a human is preferably configured not to operate at lower frequencies in order to avoid potentially interfering with cardiac functions of the patient. These lower frequency ranges typically are between 16-100 Hz.

Figure 1:
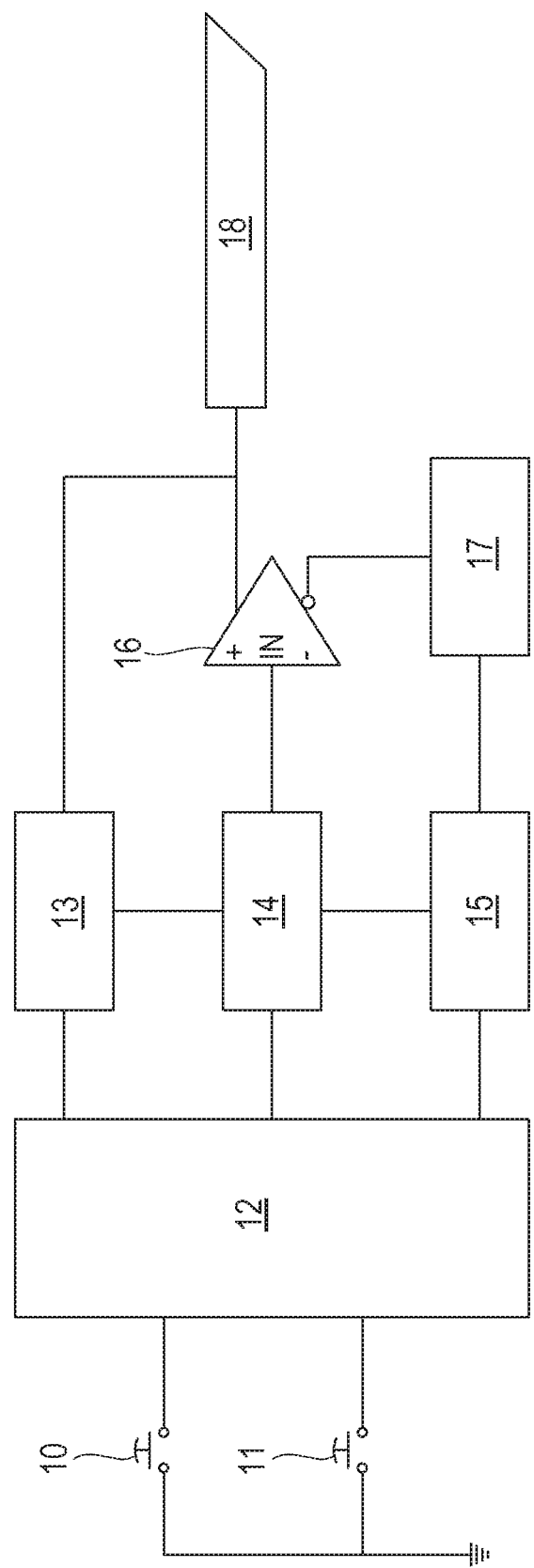
FIG. 1 is a block diagram of one embodiment of the present invention.

Referring now to FIG. 1 which shows a block diagram of one embodiment of the present invention. The cordless electronic surgical knife has a switch 10 for a specific mode of operation and a switch 11 for an additional specific mode operation. Other switches may include to control additional modes of operation. Switch 10 and switch 11 are connected to a microprocessor 12 that reads inputs from an output monitor feedback circuit 13 and a return monitor feedback circuit 15. The microprocessor 12 uses the inputs from the switches 10 and 11, the output monitor feedback circuit 13 and the return monitor feedback circuit 15 to generate a waveform that is sent to a waveform shaping circuit 14 which drives the differential amplifier circuit 16. One leg of the differential amplifier circuit 16 drives the cutting surface edge 18 of the blade. A second leg of the differential amplifier circuit 16 is connected to an electromagnetic pickup circuit 17 that provides an electrostatic return path for the current generated by the cutting surface edge 18.

All of this circuitry may be battery powered. In a typical embodiment of the invention, a high current"10C" lithium polymer or "LiPo" type battery may be used which will meet current demands of this embodiment of the invention. In other embodiments, battery technologies with higher short circuit current specifications may be used to achieve a battery size of 2-5 cm$^2$. The weight and dimensions of the battery should be considered as a factor that potentially affects the mobility and ease of use of the device by the medical personnel.

The switches 10 and 11 are connected to the microprocessor 12 and determine the mode of operation. Modes of operation are not limited to but may include cutting and coagulation. The microprocessor 12 generates a waveform at a specific frequency, pulse width, periodicity and voltage appropriate to cut or coagulate specific tissue types based on feedback received from the output monitor feedback circuit 13 and the return monitor feedback circuit 15. Further, the microprocessor 12 may vary the frequency, the current, the pulse width, the periodicity, the waveform shape, and the output voltage to ensure and maintain operation of the device to optimally cut or coagulate tissue based on the feedback received. The microprocessor 12 controls the waveform shaping circuit 14 which performs additional shaping for the waveform and provides voltage level information which amplifies or attenuates the signal level that is fed to the input of the differential amplifier circuit 16.

The differential amplifier circuit 16 has a low impedance output sufficient to provide the appropriate voltage and current to cut and coagulate tissue. One leg of the differential amplifier circuit 16 output is connected to the cutting surface edge 18 which is driven at a voltage, frequency, pulse width and periodicity or "duty cycle" (i.e., the interval that a frequency is enabled or disabled) sufficient to cut or coagulate tissue. The electromagnetic pickup circuit 17 provides a return path for the proper amount of current passing through the tissue and through the cutting surface edge 18 and is tuned to a resonant frequency preferably matched to the frequency of the cutting surface edge 18.

The output monitor feedback circuit 13 provides zero-crossing data for time analysis and amplitude data to the microprocessor 12. In alternative embodiments of the invention, the output monitor feedback circuit 13 controls the waveform shaping circuit 14 directly. In other embodiments, the feedback circuit may detect different tissue types and adjust voltage and current appropriately.

Figure 2:
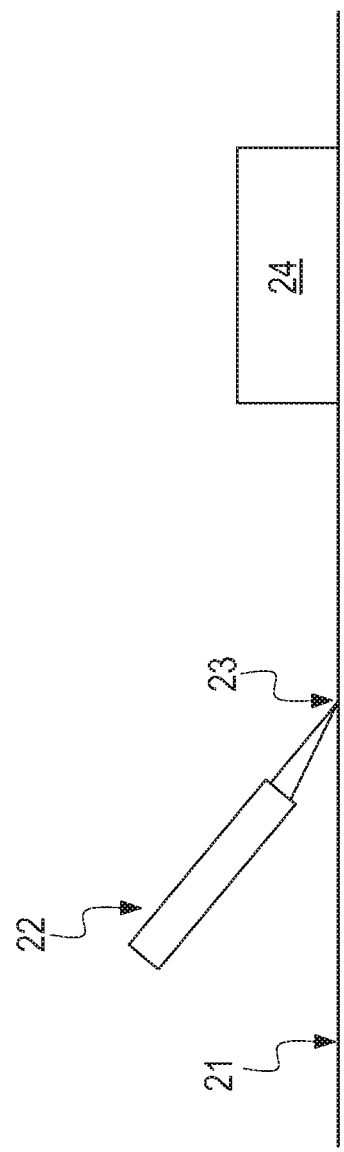
FIG. 2 is a side view of the components in use of one embodiment of the present invention.

Referring now the FIG. 2 which shows is a side view of the components in use of one embodiment of the present invention, the circuitry described with respect to FIG. 1 is housed within a surgical knife 22. The cutting edge of the surgical knife 22 makes contact with tissue 21 when in use. The circuitry within the surgical knife 22 preferably drives the cutting edge at a voltage, frequency, pulse width, periodicity and voltage sufficient to cut or coagulate the tissue 21 at the incision point 23. The current is electro-statically coupled to the surgical knife 22 and additional electrostatic coupling, if required, is provided by a signal amplifier 24 that is affixed to the tissue 21.

Figure 3:
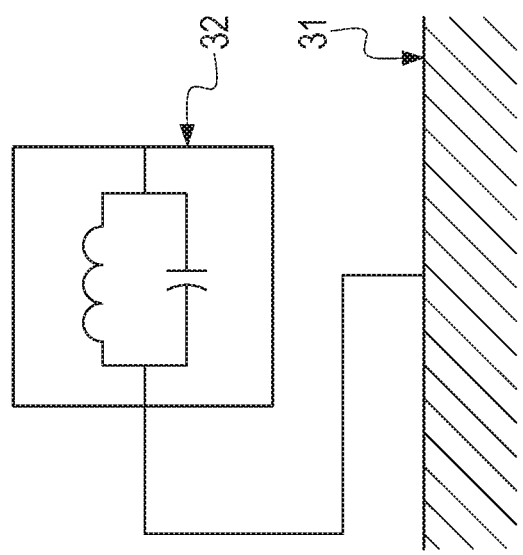
FIG. 3 is a schematic circuitry diagram of a passive tissue pad signal amplifier in use of one embodiment of the present invention.
Figure 4:
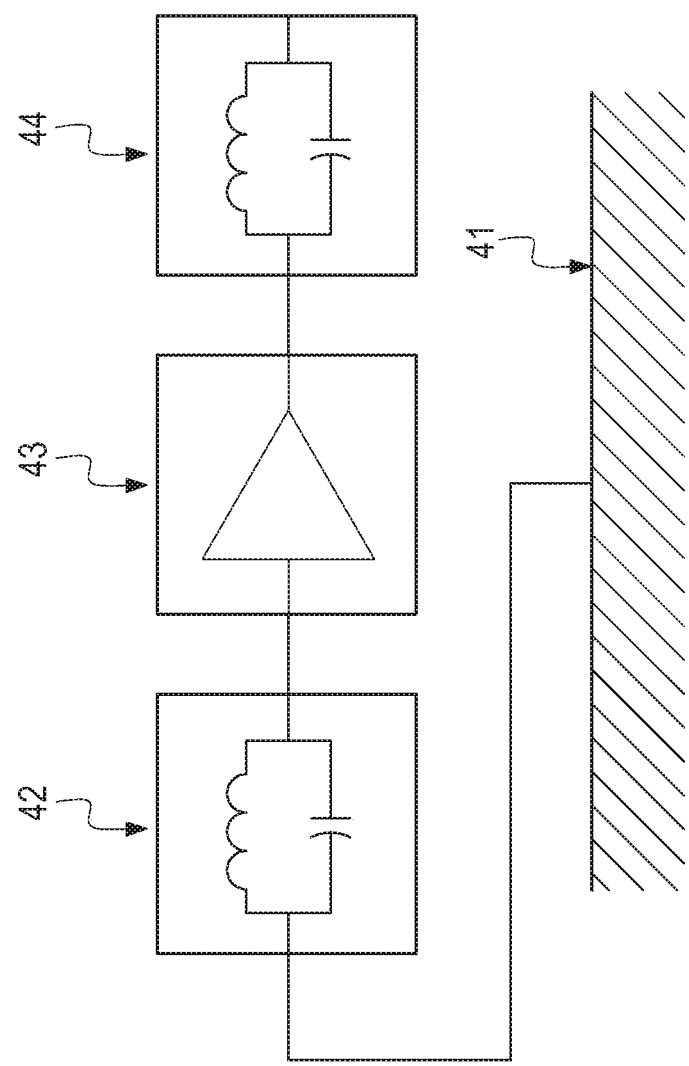
FIG. 4 is a schematic circuitry diagram of an active tissue pad signal amplifier in use of one embodiment of the present invention.

The signal amplifier 24 makes electrical contact with the surface of the tissue and is connected to a tuned circuit that is resonant at the frequency of the cutting surface edge 18. This provides a strong electrostatic coupling with the electromagnetic pickup circuit 17 providing a path for current to flow from the cutting surface edge 18 through the tissue 21 and creating a cutting or coagulating action. In other embodiments of the invention, the signal amplifier 24 increases the coupling with the electromagnetic pickup circuit 17. Referring back to FIG. 1, the electromagnetic pickup circuit 17 may include a plurality of axes to improve electrostatic coupling while the instrument 22 is moved in various positions relative to the surface of the tissue 21 and/or the signal amplifier 24. FIG. 3 shows a schematic circuitry diagram of a passive tissue pad signal amplifier for use in one embodiment of the present invention. This amplifier includes a tuned circuit 32 in contact with the tissue 31, preferably tuned to match the frequency of the cutting edge 18. In an alternative embodiment, FIG. 4 shows a schematic circuitry diagram of an active tissue pad signal. This amplifier includes two tuned circuits 42 and 44 and an amplifier 43 in contact with the tissue 41.

The construction of the invention as shown in FIG. 1 and FIG. 2 include an electronic circuit, battery and cutting edge contained in a single enclosure that electro-statically couples with tissue or an affixed signal amplifier but may also be embodied as an electronic circuit, battery and cutting edge that connects directly from the common of the surgical knife 22 through a small gauge conductive wire to a conductive pad affixed to the tissue 31 or to the open node of the tuned circuit 32 to provide efficient current transfer to complete the circuit.

Advantages of some embodiments of the invention include, without limitation, a surgical instrument that cuts and coagulates tissue without the inclusion of an attached cable, is easier to maneuver during surgical procedures, allows faster surgical procedures by eliminating the need to adjust for an attached cable and is similar to standard metal cutting instruments. In other embodiments, a cord may be used but teachings of the present invention allow for a surgical instrument with a shorter length cable, or a smaller diameter cable that is more easily maneuvered.

Figure 5:
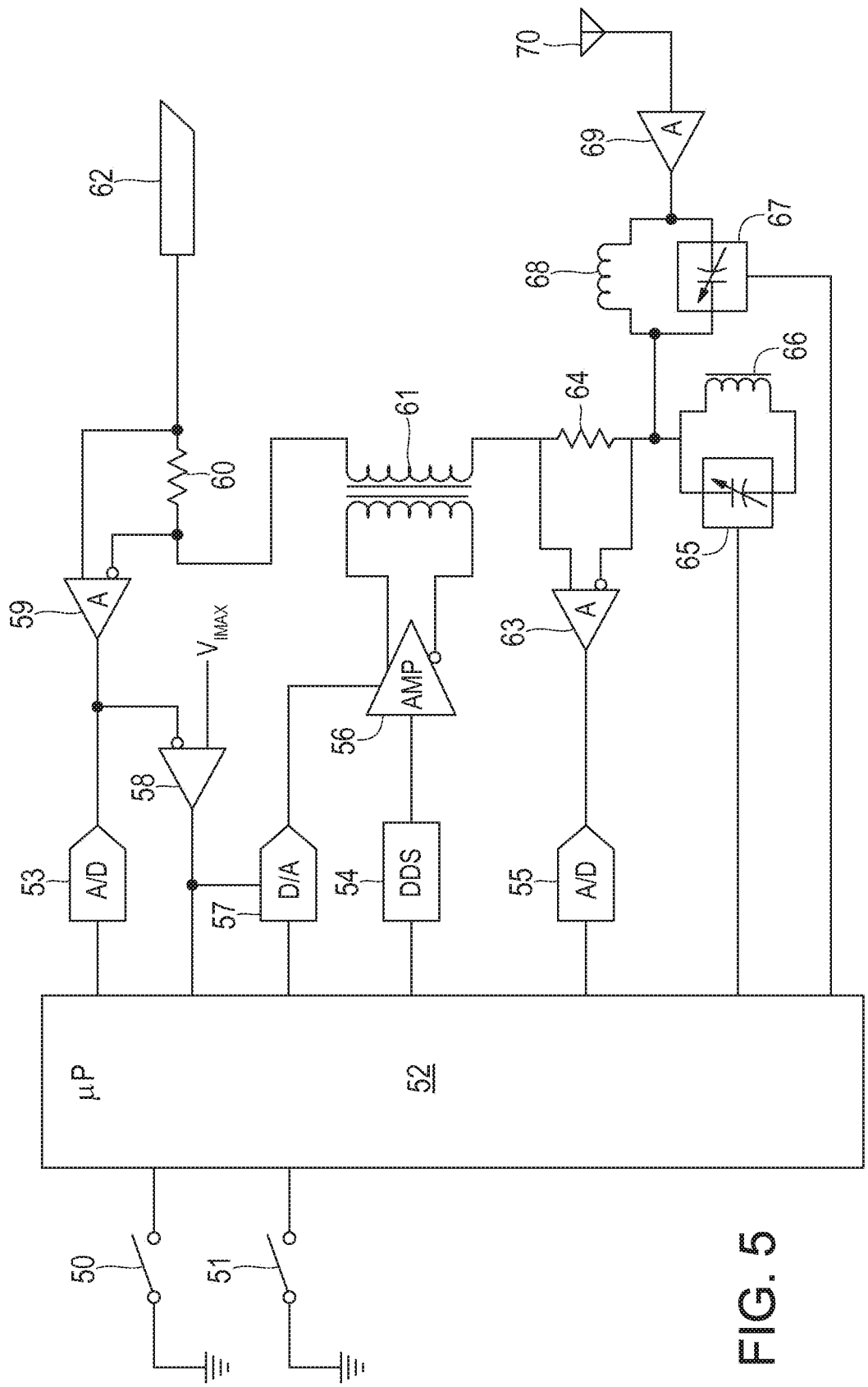
FIG. 5 is a schematic circuitry diagram that shows details of the FIG. 1 block diagram for one embodiment of the present invention.

FIG. 5 shows certain details of the circuitry illustrated in FIG. 1. In this embodiment, a cordless electronic surgical knife has a first switch 50 for a coagulation mode of operation and a second switch 51 for a cutting mode operation. The second switch 51 instructs a microprocessor (µP) 52 to output a continuous wave carrier for the duration of its closure while the first switch 50 instructs the microprocessor 52 to output a continuous wave carrier that is varied in pulse width or duty cycle or alternatively varies the periodicity of a continuous wave carrier using on-off keying to create short burst of the carrier wave output signal. "On-Off Keying" is defined as periodically enabling or disabling the waveform. This is primarily used in the coagulation mode to reduce the effective power by turning the wave on and off at the desired duty cycle.

Pulse-width or duty cycle modulation may be suitable for low frequency operation while on-off keyed frequency pulses are typically suited for higher frequency operation. Other switches may be included to control additional modes of operation.

The microprocessor 52 controls the output carrier frequency of the device by either generating it internally, driving the input of the carrier signal amplifier (AMP) 56 directly or (as shown in FIG. 5) creating the carrier frequency by sending a digital signal to a direct digital synthesizer (DDS) 54 which drives the carrier signal amplifier 56. The output of the carrier signal amplifier 56 drives a step-up transformer 61 to achieve the desired output voltage that is ultimately applied to the cutting edge knife 62 and the "return path pickup circuit" that includes a tuned circuit pickup elements 65, 66 and/or an antenna with tuned circuit elements 70, 69, 68, 67.

The microprocessor 52 reads inputs from an "output monitor feedback circuit" through an analog to digital converter (A/D) 53 that is connected to a voltage amplifier (A) 59, which is measuring the voltage induced across a low value resistor 60. The output of the voltage amplifier 59 is also connected to a voltage comparator 58, which if the output current exceeds a threshold determined by the voltage VImax, outputs a digital signal to disable the digital-to-analog output level controller (D/A) 57 and is also read by the microprocessor 52. This provides an adjustable mechanism to prevent current levels that may present discomfort to the patient and/or prevent damage to the device.

A "return monitor feedback current" is read by the microprocessor 52 through a circuit made of a low value resistance 64 connected to a voltage amplifier (A) 63, which is connected to an analog-to-digital converter (A/D) 55. The output current and return current values are used by the microprocessor 52 to adjust the output voltage presented to the cutting edge 62 by adjusting the voltage presented to the voltage controlled amplifier 56 fed by a digital-to-analog voltage converter 57. In surgical applications, the voltage presented to the cutting edge 62 should be sufficient to maintain an appropriate current through the tissue for cutting or coagulation.

As tissue impedance may vary or the feedback path coupling may vary, the output voltage is varied to maintain the desired current through the tissue. The return path for the cutting and coagulation current is accomplished by using a variety of methods to enhance power transfer efficiency. A tuned circuit intended for RF electromagnetic coupling in frequencies ranging from VLF to UHF includes a tuned capacitor 65 (which may be a digitally tuned capacitor) and a pickup inductor 66 to capture the return path signal. This signal is fed to the current sense resistor 64 which in turn is coupled to the output of the step-up transformer 61. In addition, a metal plate (not shown) may be attached to the open side of the tuned circuit including the tuned capacitor 65 and the pickup inductor 66 to provide an additional capacitive coupled return path.

The microprocessor 52 adjusts the frequency of the tuned circuit by adjusting the digitally tuned capacitor 65 to a value appropriate for the selected operating frequency. For frequencies in the GHz range, an antenna 70 provides a return path and is connected to a unity-gain broadband amplifier (A) 69 that feeds a tuned circuit comprising of a tuned capacitor 67 (which may be a digitally tuned capacitor) and an inductor 68. The unit-gain broadband amplifier 69 may be eliminated in other embodiments of the device to provide a straight return path to the tuned circuit including the tuned capacitor 67 and inductor 68.

In an alternative mode of operation shown in FIG. 5, this embodiment of the present invention is capable of detecting an optimum operating frequency among several selectable bands, which may be selected by the user with an additional switch coupled to the microprocessor 52. Different tissues in the body such as liver, fat, muscle, etc., are known to have different resonant frequencies. However, resonant frequencies of a specific tissue type can vary from patient to patient. This embodiment of the present invention can determine the resonant frequency of a specific tissue of a specific patient by injecting a variable frequency to the carrier signal amplifier 56 and monitor for a signal peak from the return path analog-to-digital converter 55. The optimum operating frequency may also be determined by injecting broadband noise into the carrier signal amplifier 56, and applying a Fast Fourier Transform (FFT) on the input data of the return path analog-to-digital converter 59 to determine a peak or resonant frequency of the tissue. The FFT algorithm is similar or equivalent to common spectrum analyzer algorithms that provide amplitude versus frequency plots across a particular frequency range. Once a resonant frequency is determined for a desired tissue to be cut or cauterized, the function of the device can be impeded once the blade is no longer in contact with that type of tissue. In alternative embodiments, if a resonant frequency of a non-desired tissue type is determined, the function of the blade may be limited to all tissue except the non-desired type. For example, if a procedure is desired for tissue surrounding a bone, the function of the blade may be limited to all operating frequencies that are non-resonant to the bone. Once contact is made with bone tissue, the operation of the blade stops in order to limit damage to the bone.

Figure 6:
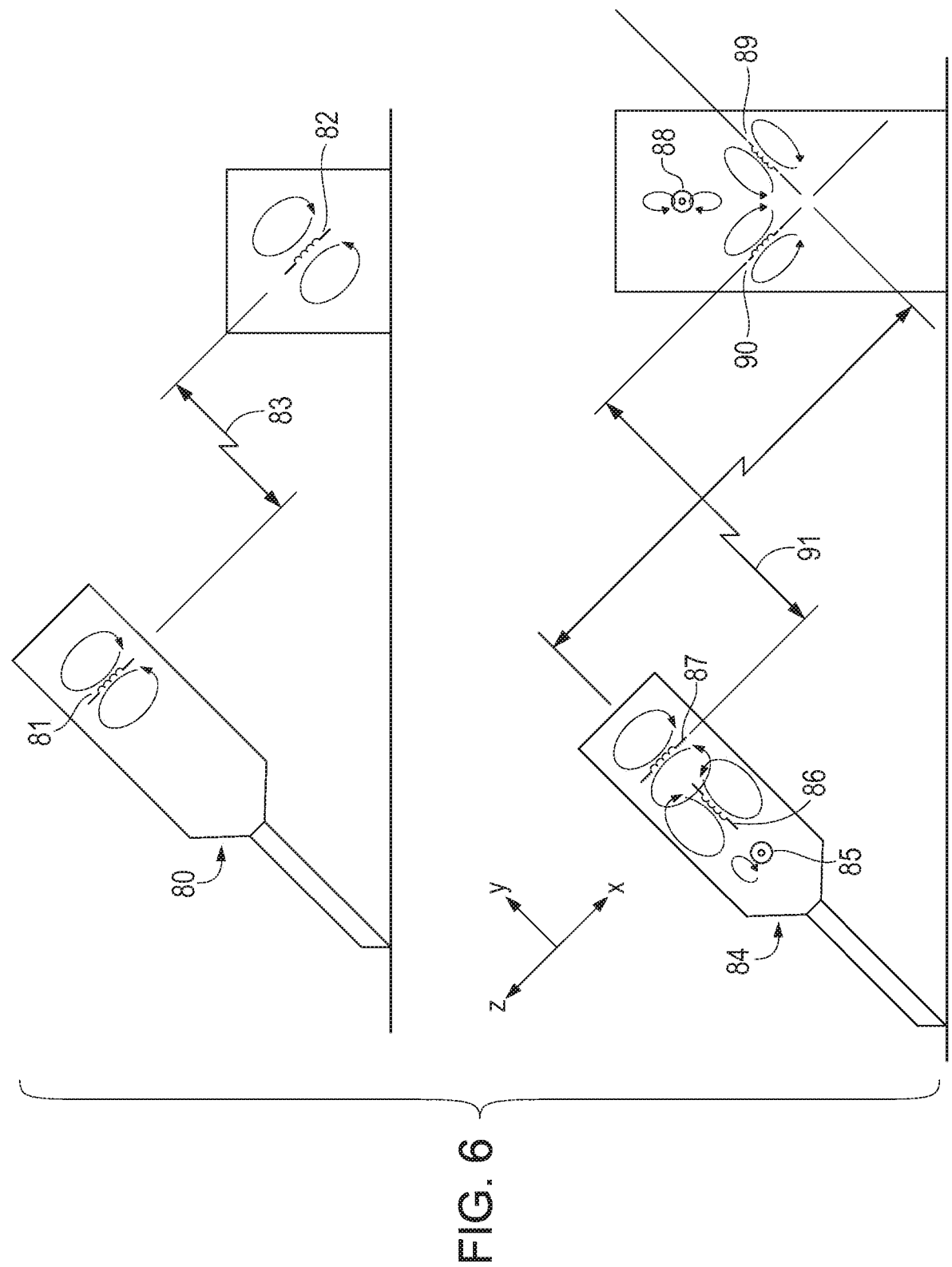
FIG. 6 shows a diagram of electromagnetic coupling between the surgical knife and the transmitting antenna that is attached to the tissue of the patient for one embodiment of the present invention.

The embodiment of the present invention in FIG. 6 shows methods for electromagnetic coupling between a surgical knife 80 and a transmitting antenna or inductor 82 enclosed in the signal amplifier 24 device (shown in FIG. 2) that may be attached to the tissue of the patient. The signal amplifier 24 may either actively amplify the signal or the signal may be radiated passively without additional amplification. Proper alignment of the polarization of the receiving antenna or inductor of the surgical knife 80 with the transmitting antenna or inductor 82 increases electromagnetic signal transfer 83. During use, the surgical knife 80 is moved in varying positions providing a less than optimum return path. The surgical knife 80 can increase the voltage to make up for this signal loss.

Another embodiment of the invention also shown in FIG. 6 includes antenna or inductors that are polarized in the x, y and z planes. A surgical knife 84 may contain an antenna or inductor aligned in the x-plane 87, and antenna or inductor in the y-plane 86, and an antenna inductor in the z-plane 85. The signal amplifier 24 device also may include a transmitting antenna or inductors in the x-plane 90, the y-plane 89 and z-plane 88. This reduces the voltage requirements for the surgical knife 84 to compensate for the return path polarity misalignment resulting from normal movement and use of the surgical knife 84.

Figure 7:
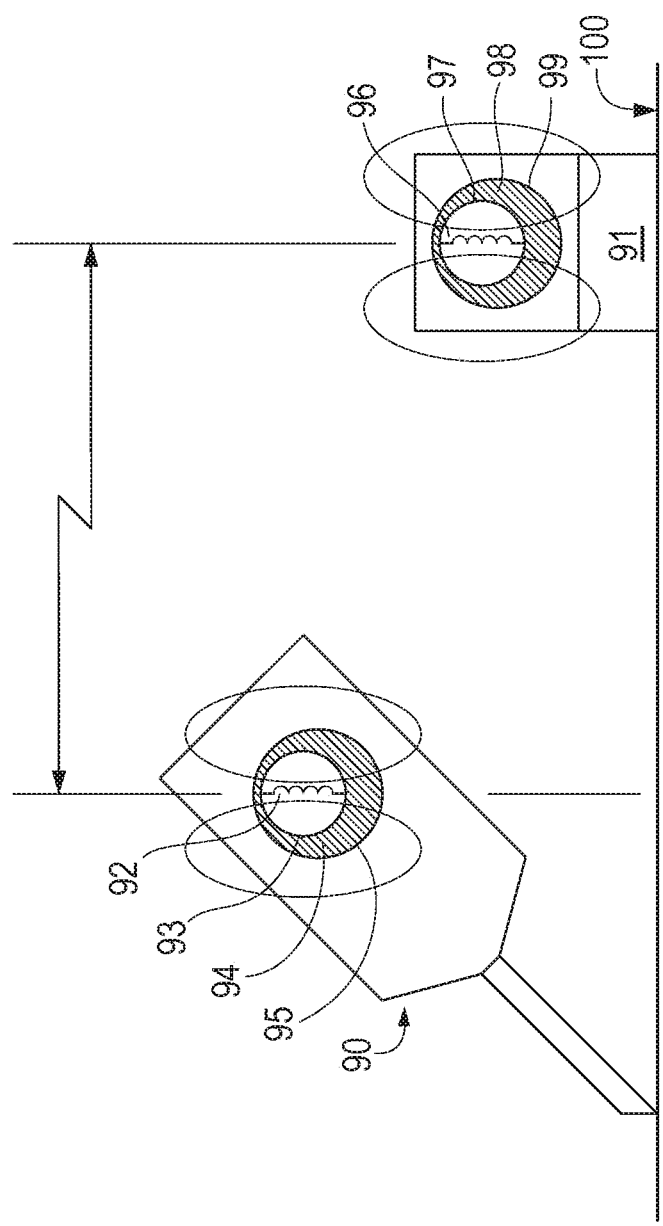
FIG. 7 shows an alternative embodiment of the invention that uses gravity to align the polarization of the receiving and transmitting antennas.

FIG. 7 shows another embodiment of the present invention that uses gravity to align the polarization of the receiving and transmitting antennas or inductors. A surgical knife 90 houses an element that contains an inductive receiving element 92 that is encapsulated in an inner enclosure such a hollow inner sphere 93. The inductive element 92 is floating in a liquid material 94 which in turn is encapsulated in an outer enclosure such as an outer sphere 95. The liquid should have a low enough viscosity to track the surgeon's knife movement during use. The encapsulated inductive receiving element is connected by two flexible insulated wires. The inner sphere 93 is weighted so that polarization of the receiving element 92 is aligned with the earth's gravity regardless of the position of the surgical knife 90. A signal amplifier 91, which is attached to the surface of the patient tissue 100, houses a similar element that contains the inductive receiving element 96 that is encapsulated in an inner enclosure such as an inner sphere 97 which is floating in a liquid material 98 which in turn is encapsulated in an outer enclosure such as an outer sphere 99. The inner sphere 97 is weighted such that the polarization of the transmitting element 96 is aligned with the earth's gravity regardless of the position or placement of the signal amplifier 91 thereby ensuring alignment between the receiver element 92 and transmitting element 96 and provides an optimum return path for the device.

Figure 8:
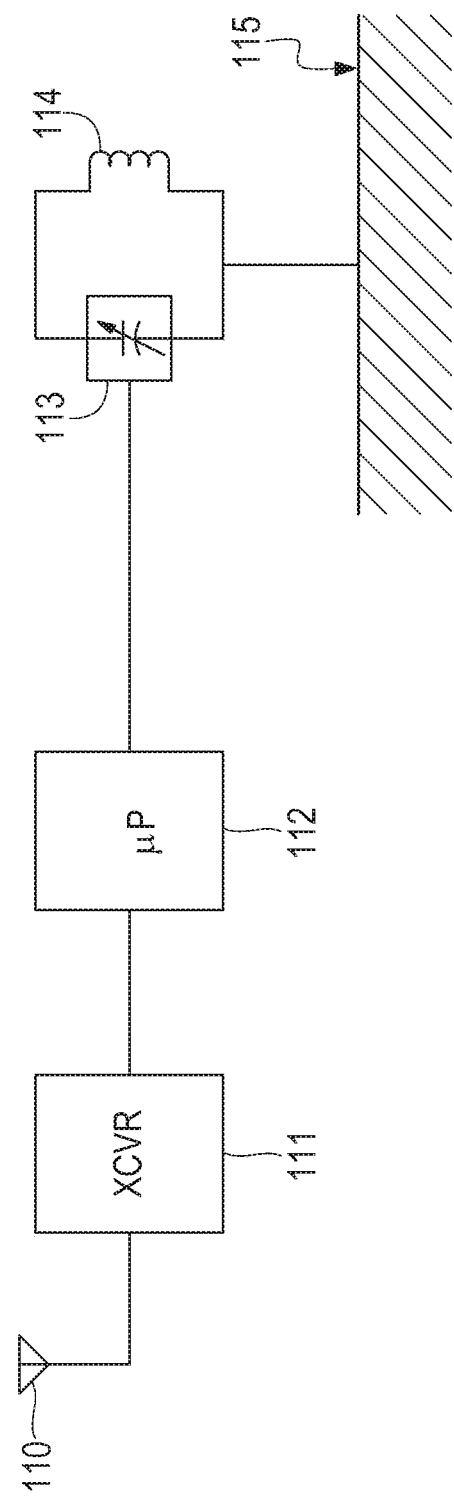
FIG. 8 shows which shows an alternative embodiment of the invention with a signal amplifier used for varying cutting frequencies.

FIG. 8 shows another embodiment of the present invention with a signal amplifier used for varying cutting frequencies. In this embodiment, the signal amplifier used for varying cutting frequencies is affixed to the tissue of the patient through a conductive pad 115 that includes an antenna 110 and a transceiver (XCVR) 111 that receives operating frequency commands from the surgical knife. The commands ensure that the signal amplifier is tuned to the same frequency as the surgical knife to facilitate maximum power transfer. The frequency change command signal sent from the surgical knife is received by the antenna 100 and demodulated by the transceiver 111. The demodulated signal is read by a microprocessor 112 which sends a signal to the variably tuned capacitor 113 that changes the resonant frequency of the tuned circuit with the inductor 114. The signal is transferred from a conductive pad 115 affixed to the patient. The microprocessor 112 sends an acknowledgement command to the transceiver 111 which transmits the signal to the antenna 110 which is detected and decoded by the surgical knife.

While the invention has been described with respect to a limited number of embodiments, those skilled in the art, having benefit of this disclosure, will appreciate that other embodiments can be devised which do not depart from the scope of the invention as disclosed here. The foregoing description is therefore considered in all respects to be illustrative and not restrictive. Therefore, the present invention should be defined with reference to the claims and their equivalents, and the spirit and scope of the claims should not be limited to the description of the preferred embodiments contained herein.

We claim:

1. A surgical apparatus comprising:
    a blade with an edge for contacting tissue of a patient, where the blade is operably coupled to a receiving antenna;
    a signal amplifier for placing in electrical contact with tissue of said patient and with a transmitting antenna that transmits a wireless signal to the receiving antenna at a certain frequency and waveform;
    an output monitor feedback circuit that monitors frequency and amplitude data of an RF signal from a differential amplifier circuit;
    a return monitor feedback circuit that monitors frequency and amplitude data from the tissue of the patient; and
    a microprocessor that receives the frequency and amplitude data from the output monitor and from the return monitor and adjusts at least one of a voltage, the frequency, and waveform of the RF signal provided by the differential amplifier.

2. The apparatus of claim 1, where the transmitting antenna comprises at least two separate inductive circuits aligned on different planes with respect to one another.

3. The apparatus of claim 2, where the transmitting antenna comprises three inductive circuits that are respectively aligned in x, y and z planes.

4. The apparatus of claim 1, where each of the transmitting antenna and the receiving antenna is encapsulated inside an enclosure floating in a liquid material so that each antenna is aligned by gravity.

5. A surgical apparatus comprising:
    an enclosure and a blade extending from said enclosure, said blade with an edge for contacting tissue of a patient, said enclosure containing:
    a differential amplifier circuit configured to provide an RF signal having a voltage and a current to said blade at a certain frequency and waveform;
    an output monitor feedback circuit that monitors frequency and amplitude data from the differential amplifier circuit associated with said RF signal;
    a receiving antenna that is operable to receive a wireless signal from tissue of said patient, wherein said wireless signal contains frequency and amplitude data from the tissue associated with said RF signal;
    a return monitor feedback circuit that monitors the frequency and amplitude data in said wireless signal; and
    a microprocessor that receives the frequency and amplitude data from the output monitor and from the return monitor and adjusts at least one of the voltage, frequency and waveform of said RF signal provided by the differential amplifier.

6. The surgical apparatus of claim 5, wherein said receiving antenna comprises at least two inductive circuits, wherein the at least two inductive circuits are aligned on different planes.

7. The surgical apparatus of claim 6, wherein said receiving antenna comprises three inductive circuits, wherein each inductive circuit is aligned on a plane that is approximately orthogonal to the other two inductive circuits.

8. The surgical apparatus of claim 5, wherein said receiving antenna comprises an inductive element disposed in an antenna enclosure, wherein said antenna enclosure is configured to maintain said inductive element in a constant orientation relative to the direction of gravitational forces.

9. The surgical apparatus of claim 5, wherein said receiving antenna comprises:
    an outer antenna enclosure containing a liquid;
    an inner antenna enclosure disposed in said outer antenna enclosure, wherein said inner antenna enclosure is weighted at one end; and
    at least one inductive element disposed in said inner antenna enclosure.

10. The surgical apparatus of claim 5, wherein said receiving antenna is operable to receive said wireless signal from a transmitting antenna in electrical contact with tissue of said patient.

11. The surgical apparatus of claim 5, wherein said differential amplifier circuit, said output monitor feedback circuit, said return monitor feedback circuit, and said microprocessor are powered by a battery contained within said enclosure.

12. The surgical apparatus of claim 5, wherein the microprocessor adjusts the voltage, frequency, and waveform provided by the differential amplifier through a waveform shaping circuit.

13. The surgical apparatus of claim 5, wherein an initial voltage, frequency, and waveform is associated with operating the blade in a coagulation mode or a cutting mode.

14. A surgical system comprising: a transmitting antenna for placing in electrical contact with tissue of a patient; and an enclosure and a blade extending from said enclosure, said blade with an edge for contacting tissue of a patient, said enclosure containing: a differential amplifier circuit configured to provide an RF signal having a voltage and a current to said blade at a certain frequency and waveform; and a receiving antenna that is operable to receive a wireless signal from said transmitting antenna, wherein said wireless signal contains frequency and amplitude data from said tissue associated with said RF signal; wherein said enclosure further comprises: an output monitor feedback circuit that monitors frequency and amplitude data from the differential amplifier circuit associated with said RF signal; a return monitor feedback circuit that monitors the frequency and amplitude data in said wireless signal; and a microprocessor that receives the frequency and amplitude data from the output monitor and from the return monitor and adjusts at least one of the voltage, frequency and waveform of said RF signal provided by the differential amplifier.

15. The surgical system of claim 14 further comprising: a signal amplifier for placing in electrical contact with tissue of said patient, wherein said transmitting antenna is in electrical contact with said tissue through said signal amplifier.

16. The surgical system of claim 15, wherein said signal amplifier comprises a first transceiver, wherein said enclosure further comprises a second transceiver operably connected to said microprocessor, and wherein said microprocessor is operable to transmit from said second transceiver to said first transceiver a signal to adjust the frequency of said signal amplifier.

17. The surgical system of claim 14, wherein said receiving antenna comprises at least two receiving inductive circuits aligned on different planes, and wherein said transmitting antenna comprises at least two transmitting inductive circuits aligned on different planes.

18. The surgical system of claim 17, wherein said receiving antenna comprises three receiving inductive circuits and each receiving inductive circuit is aligned on a plane that is approximately orthogonal to the other receiving inductive circuits, and wherein said transmitting antenna comprises three transmitting inductive circuits and each transmitting inductive circuit is aligned on a plane that is approximately orthogonal to the other transmitting inductive circuits.

19. The surgical apparatus of claim 14, wherein each of said receiving and transmitting antennas comprises an inductive element disposed in an antenna enclosure, wherein each of said antenna enclosures is configured to maintain the respective inductive element in a constant orientation relative to the direction of gravitational forces.

20. The surgical apparatus of claim 14, wherein each of said receiving and transmitting antennas comprises:
an outer antenna enclosure containing a liquid;
an inner antenna enclosure disposed in said outer antenna enclosure, wherein said inner antenna enclosure is weighted at one end; and
at least one inductive element disposed in said inner antenna enclosure.

* * * * *